United States Patent [19]

Kenney

[11] Patent Number: 5,059,398
[45] Date of Patent: Oct. 22, 1991

[54] DISPOSABLE PRESELECTED-VOLUME CAPILLARY PIPET DEVICE

[75] Inventor: James W. Kenney, West Chester, Pa.

[73] Assignee: Drummond Scientific Company, Broomall, Pa.

[21] Appl. No.: 757,608

[22] Filed: Jul. 22, 1985

[51] Int. Cl.$^5$ ............................................. B01L 3/02
[52] U.S. Cl. .................................. 422/100; 422/101; 73/864.02; 73/864.13; 436/180; 222/249; 222/250
[58] Field of Search ............................. 422/100, 101; 73/864.02, 864.13; 436/180; 222/249, 250

[56] References Cited

U.S. PATENT DOCUMENTS

| | | |
|---|---|---|
| 1,678,540 | 7/1928 | Trenner . |
| 2,423,173 | 7/1947 | Brady et al. . |
| 2,685,800 | 8/1954 | Natelson . |
| 2,855,928 | 10/1958 | Reynolds . |
| 2,974,528 | 3/1961 | Sanz . |
| 3,045,494 | 7/1962 | Gerarde . |
| 3,285,296 | 11/1966 | Ishimaru et al. . |
| 3,406,573 | 10/1968 | Burke . |
| 3,500,689 | 3/1970 | Band . |
| 3,734,358 | 5/1973 | Bergeron . |
| 3,741,732 | 6/1973 | Stanfield . |
| 3,811,360 | 5/1975 | Jurado . |
| 3,864,979 | 2/1975 | Ayres ............................ 422/100 X |
| 3,864,979 | 2/1975 | Ayres . |
| 3,891,392 | 6/1975 | Belts et al. ..................... 436/180 X |
| 3,891,392 | 6/1975 | Betts et al. . |
| 3,985,032 | 10/1976 | Avakian ........................ 422/101 X |
| 4,104,025 | 8/1978 | Retzer . |
| 4,178,803 | 12/1979 | Lee ................................ 222/309 X |
| 4,267,729 | 5/1981 | Eddelman et al. . |
| 4,424,817 | 1/1984 | Williams . |
| 4,483,825 | 11/1984 | Fatches ........................... 422/100 |

*Primary Examiner*—Robert J. Warden
*Assistant Examiner*—Lynn M. Kummert
*Attorney, Agent, or Firm*—John F. A. Earley; John F. A. Earley, III

[57] ABSTRACT

A disposable preselected-volume capillary pipet device comprises a capillary tube having an admitting emitting end for liquids and a vent end for passing air from the tube as the liquid is being drawn into the tube by capillary action, a port at the admitting-emitting end for admitting and emitting liquids to the capillary tube, a port at the vent end of the tube for passing air freely from the tube, a barrier plug for passing air and stopping the passage of liquid through the tube, with the barrier plug being positioned in the tube at a preselected distance from the admitting-emitting port to define a liquid chamber of preselected volume, and a plunger for pushing the barrier plug from the vent end to push the preselected volume of liquid out of the liquid chamber. The barrier plug may be mounted in the tube or in the head of the plunger. The method includes admitting a volume of liquid to be tested into the capillary tube by capillary action, venting the air in the tube through the barrier plug and the vent end during the admitting of the liquid into the capillary tube by capillary action, stopping the admitting of the liquid when the liquid contacts the wets the barrier plug to obtain a preselected volume of liquid in the chamber, and discharging the liquid from the chamber by pushing the barrier plug through the chamber.

16 Claims, 1 Drawing Sheet

– 1 –

DISPOSABLE PRESELECTED-VOLUME CAPILLARY PIPET DEVICE

BACKGROUND OF THE INVENTION

1. Technical Field

This invention is in the field of liquid handling, and more specifically is in the field of disposable capillary pipet devices for picking up and transferring a selected volume of liquid such as blood from one point to another for testing.

2. Background of the Prior Art

Capillary pipet devices are known for transferring liquids such as a specimen of blood from a patient to a test tube or testing apparatus. A drop of blood is produced by sticking the finger of a patient with a needle, the blood is picked up by a pipet and is taken to a machine where the blood is tested and analyzed. Capillary tubes are excellent for drawing blood from this drop because the capillary tubes suck the blood up into the tubes at a speed that does not also draw up air bubbles, which are undesireable.

However, a problem arises in trying to eject the blood from the capillary tube. It is conventional to provide a rubber bulb that fits over the vent end of the capillary tube, which is away from the liquid intake and emission end. To eject the liquid from the tube, the operator places a finger over a hole in the top of the bulb and squeezes the bulb to force air against the liquid and push the liquid out of the tube. However, the liquid bubbles at the end and the last drop of liquid is always hard to get out. It may be possible to get the last drop out of the tube by shaking but this is messy and the last drop may not go where desired. In any event, prior methods do not deliver a precise volume of blood to a testing machine, and without a precise volume of blood the testing machine cannot perform its tests accurately.

SUMMARY OF THE INVENTION

The objects of this invention are to provide a pipet which is disposable, inexpensive, and accurate in delivering a preselected volume of liquid for testing, and to provide method and apparatus which overcome the prior art problem of delivering the last drop of liquid.

The objects of the invention are accomplished by providing a capillary tube for drawing liquid into the tube by capillary action, with the tube having an admitting-emitting end and a vent end, hydrophobic barrier means positioned in the capillary tube for passing air through to the vent end and preventing the passage of liquid, and piston means for pushing the barrier means to discharge a preselected volume of liquid out of the capillary tube in order to deliver the liquid to testing apparatus. The method includes admitting a volume of liquid to be tested to capillary tube by capillary action, venting the air in the tube through the barrier means during the admitting of the liquid, stopping the admitting of the liquid when it contacts and wets the barrier means, and discharging the liquid to testing apparatus by pushing the barrier means through the capillary tube to push the liquid out of the tube.

DETAILED DESCRIPTION

Figure 1:
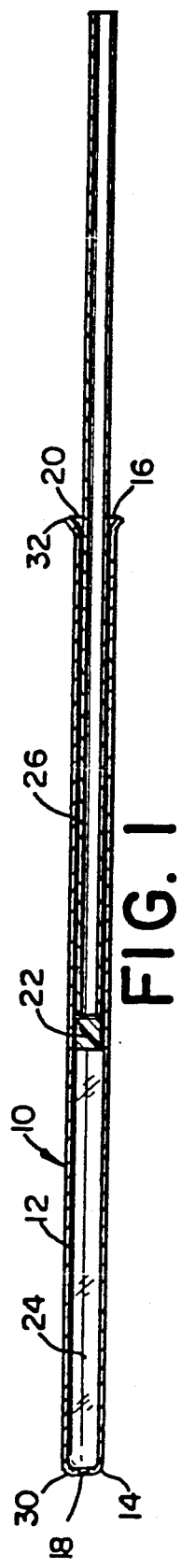
FIG. 1 is a view in vertical section of a disposable preselected-volume capillary pipet device constructed in accordance with this invention and includes a hollow tube plunger.

Turning now to the drawings, there is shown a disposable preselected-volume capillary pipet device 10 for taking a preselected volume of liquid, such as blood from a patient, and delivering it to a test tube or testing apparatus.

Capillary pipet device 10 comprises a capillary tube 12, preferably made of glass, having an intake emission, or admitting-emitting end 14 for admitting a liquid and discharging it, and a vent end 16 for passing air from tube 12 as liquid is being drawn into the tube by capillary action. A port 18 is formed at admitting emitting end 14 for admitting and emitting liquids to and from the capillary tube 12, and a vent port 20 is formed at the vent end of tube 12 for passing air freely from the tube.

Barrier means 22 is provided for passing air through the tube 12 to the vent end 16 and for stopping the passage of liquid, and is positioned in tube 12 at a preselected distance from admitting-emitting port 18 to define a liquid chamber 24 of preselected volume.

Piston means is provided for pushing barrier means 22 to port 18 to push the preselected volume of liquid out of chamber 24 and deliver it to testing apparatus. The piston means comprises a plunger 26 which is preferrably a glass capillary tube of smaller outside diameter than the inside diameter of tube 12. Being hollow, plunger 26 does not impede the venting of air from tube 12 and may be positioned inside tube 12 during the capillary action of filling chamber 24 with liquid.

Figure 2:
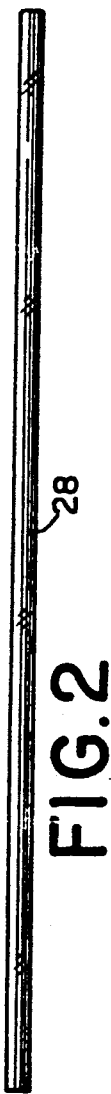
FIG. 2 is a view in side elevation of a solid rod which may be used as the plunger in the pipet device of FIG. 1.

FIG. 2 shows an alternative plunger 28 which is a solid glass rod that may be used to push barrier means 22 and the liquid from chamber 24 after the chamber has been filled. However, plunger 28 may not be positioned in tube 12 during the filling operation because it would prevent the venting of air from tube 12.

Port 18 is provided with a stop shoulder 30 that flares inwardly to stop the barrier means 22 from discharging from tube 12 when the piston means pushes it through the tube.

The barrier means 22 is made of a hydrophobic material that passes air freely to vent it from tube 12 so as to not impede or slow down the capillary action of drawing the liquid into the tube. Barrier means 22 also stops passage of air and liquid upon being contacted by the liquid after chamber 24 has been filled with a preselected volume of the liquid.

Vent port 20 is provided with a flange 32 that flares outwardly for easy insertion of the barrier means 22 and the piston means.

Figure 3:
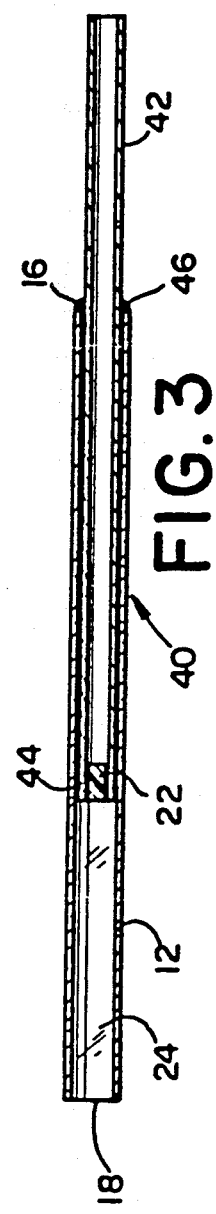
FIG. 3 is a view in vertical section of another embodiment of the invention.
Figure 4:
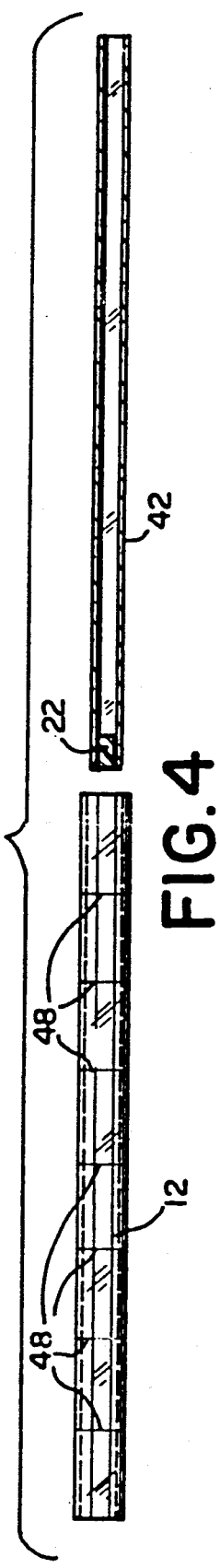
FIG. 4 is a view of the pipet device of FIG. 3 in disassembled condition.

Turning to the embodiment of the invention shown in FIGS. 3 and 4, there is shown a disposable preselected volume capillary pipet device 40 wherein the piston means comprises a plunger 42, a tube preferably of glass, positioned in capillary tube 12 with the barrier means 22 being positioned in head end 44 of plunger 42.

As shown in FIG. 3, a wax seal 46 may be used to connect the plunger 42 to the vent end 16 of the capillary tube 12 to temporarily hold the barrier means 22 in desired position in capillary tube 12 during the filling operation. When chamber 24 is filled with liquid, the wax seal 46 is easily broken by the action of pushing plunger 42 toward port 18.

The method of preparing a liquid sample for testing comprises the steps of providing a capillary tube 12 having an admitting-emitting end 14 for passing liquid and a vent end 16 for passing air, and a barrier means 22 positioned between ends 14 and 16 to define a preselected volume of liquid in the chamber 24 formed between barrier means 22 and admitting-emitting end 14, venting the air in tube 12 through the barrier means 22 and the vent end 16 during the admitting of the liquid into the capillary tube 12 by capillary action, stopping the admitting of liquid when the liquid contacts and wets the barrier means 22 to obtain a preselected volume of liquid in the chamber 24, and discharging the liquid from chamber 24 by pushing the barrier means 22 through chamber 24.

The barrier means 22 may be located in tube 12 as shown in FIG. 1, or it may be located in head end 44 of plunger 42, as shown in FIGS. 3 and 4.

The capillary pipet device 10, of FIG. 1, is assembled by the manufacturer who precisely positions barrier means 22 in tube 12.

The capillary pipet device 40, of FIGS. 3 and 4, may be assembled by the manufacturer as shown in FIG. 3. However, it may also be shipped to the user in unassembled condition as shown in FIG. 4, and the user may place plunger 42 at any desired position in tube 12, using scribe marks 48 to choose the size of chamber 24 that he wants. And, of course, the user may alter the volume setting of pipet device 40 as shown in FIG. 3, if he wishes, by pushing or pulling plunger 42 to break wax seal 46, and setting plunger 42 at a desired scribe mark 48.

Hydrophobic substances suitable for use in barrier means 22 are known to the art. Barrier means 22 may be made of a hydrophobic material such as polyethylene or other type polyolefins, styrofoam aerated, light-weight multicellular polystyrene plastic, or any other plastic material which has hydrophobic characteristics, or may be a wettable material which is coated with a hydrophobic coating such as paraffin wax, beeswax or various plastics. Hydrophobic material for barrier means 22 may be obtained from Porex Technologies, 7380 Bohannan Road, Fairburn, Georgia, 30213. The hydrophobic material from Porex includes a reactive polymer, mixed with a non-reactive foamed polyethylene polymer, which gels on being wetted by an aqueous liquid such as blood to form an impervious of 14 psi or more.

I claim:

1. A method of preparing a liquid sample for testing, comprising the steps of providing a capillary means for drawing liquid into a capillary tube by capillary action, said capillary means comprising the capillary tube with an admitting-emitting end for liquids and a vent end for passing air from the tube as the liquid is being drawn into the tube by capillary action, and a barrier means positioned between the ends to define a preselected volume of liquid in a chamber formed between the barrier means and the admitting-emitting end, drawing a volume of liquid to be tested into a capillary tube by capillary action, venting the air in the tube through the barrier means and the vent end during the drawing of the liquid into the capillary tube by capillary action, stopping the drawing of the liquid when the liquid contacts and wets the barrier means to obtain a preselected volume of liquid in the chamber, and discharging the liquid from the chamber by pushing the barrier means through the chamber to the admitting-emitting end and pushing the preselected volume of liquid out of the chamber so that all of the liquid is discharged while retaining the barrier means within the tube.

2. The method of claim 1, including pushing the barrier means through the chamber by pushing a plunger against the barrier means.

3. A method of preparing a liquid sample for testing, comprising the steps of providing a capillary means for drawing liquid into a capillary tube by capillary action, said capillary means comprising the capillary tube with an admitting-emitting end for liquids and a vent end for passing air from the tube as the liquid is being drawn into the tube by capillary action, and a barrier means positioned between the ends to define a preselected volume of liquid in a chamber formed between the barrier means and the admitting-emitting end, drawing a volume of liquid to be tested into a capillary tube by capillary action, venting the air in the tube through the barrier means and the vent end during the drawing of the liquid into the capillary tube by capillary action, stopping the drawing of the liquid when the liquid contacts and wets the barrier means to obtain a preselected volume of liquid in the chamber, discharging the liquid from the chamber by pushing the barrier means through the chamber to the admitting-emitting end and pushing the preselected volume of liquid out of the chamber so that all of the liquid is discharged while retaining the barrier means within the tube, the barrier means being located in the head of a plunger formed by a hollow tube, the plunger being positioned in the capillary tube at a desired location to define the chamber of preselected volume during the capillary action of filling the chamber with liquid, and discharging the liquid from the capillary tube by pushing the plunger and the barrier means through the chamber to its end.

4. A disposable preselected volume capillary pipet device comprising capillary means for drawing liquid into a capillary tube by capillary action, said capillary means comprising the capillary tube with an admitting-emitting end for liquids and a vent end for passing air from the tube as the liquid is being drawn into the tube by capillary action, a port at the admitting-emitting end for admitting and emitting liquids to the capillary tube, a port at the vent end of the tube, barrier means for passing air freely from the tube to allow for capillary flow as the liquid is being drawn into the tube by capillary action and for stopping the passage of liquid through the tube when the liquid reaches and contacts the barrier means, said barrier means being positioned in the tube at a preselected distance from the admitting-emitting port to define a liquid chamber of preselected volume, and piston means for pushing the barrier means from the vent end to push the barrier means to the admitting-emitting end to cause the barrier means to wipe the walls of the liquid chamber and to cause the barrier means to push the preselected volume of liquid out of the liquid chamber so that all the liquid is discharged, said piston means being of sufficient length to push the barrier means to the port at the admitting-emitting end of the tube, said piston means being readily detachable from said barrier means.

5. The device of claim 4, said piston means being a plunger comprising a tube of smaller outside diameter than the inside diameter of the capillary tube.

6. The device of claim 4, said piston means being a plunger comprising a solid rod of smaller outside diameter than the inside diameter of the capillary tube.

7. The device of claim 4, including a stop shoulder flared inwardly from the admitting-emitting port to stop the barrier means from discharging from the capillary tube as the piston means pushes the liquid out of the chamber, with the interior diameter of the stop shoulder being smaller than the interior diameter of the capillary tube and being smaller than the outside diameter of the barrier means so that the stop shoulder stops passage of the barrier means from the tube.

8. The device of claim 4, said barrier means being made of a material for passing air freely to vent so as to not impede or delay the capillary action of drawing a liquid into the tube and for stopping passage of air and liquid upon being wetted by the liquid to obtain a preselected volume of liquid in the chamber.

9. The pipet device of claim 4, said piston means being a plunger adapted to pass air from the barrier means to the vent end of the capillary tube while the liquid is being drawn into the tube.

10. A disposable preselected volume capillary pipet device comprising capillary means for drawing liquid into a capillary tube by capillary action, said capillary means comprising the capillary tube with an admitting-emitting end for liquids and a vent end for passing air from the tube as the liquid is being drawn into the tube by capillary action, a port at the admitting-emitting end for admitting and emitting liquids to the capillary tube, a port at the vent end of the tube, barrier means for passing air and stopping the passage of liquid through the tube, said barrier means being positioned in the tube at a preselected distance form the admitting-emitting port to define a liquid chamber of preselected volume, and piston means for pushing the barrier means from the vent end to push the barrier means to the admitting-emitting end to wipe the walls of the liquid chamber, and to push the preselected volume of liquid out of the liquid chamber, said piston means being a plunger comprising a tube of smaller outside diameter than the inside diameter of the capillary tube, said plunger being hollow for passing air freely from said capillary tube to allow for a capillary flow, said plunger being of sufficient length to push the barrier means to the port at the admitting-emitting end of said capillary tube, said plunger being readily detachable from said barrier means, stop means at the admitting-emitting port for preventing discharging the barrier means from the tube, said stop means having a stop shoulder flared inwardly from the admitting-emitting port to stop the barrier means from discharging from the capillary tube as the piston means pushes the liquid out of the tube, said barrier means being made of a material for passing air freely to vent so as to not impede or delay the capillary action of drawing a liquid into the tube and for stopping the passage of air and liquid upon being wetted by the liquid to obtain a preselected volume of liquid in the chamber, and the vent end of the capillary tube having a flange that flares outwardly from the vent port to enlarge the vent port entrance for easy insertion of the piston means.

11. A disposable preselected volume capillary pipet device comprising capillary means for drawing liquid into a capillary tube by capillary action, said capillary means comprising the capillary tube with an admitting-emitting end for liquids and a vent end for passing air from the tube as the liquid is being drawn into the tube by capillary action, a port at the admitting-emitting end for admitting and emitting liquids to the capillary tube, a port at the vent end of the tube, barrier means for passing air and stopping the passage of liquid through the tube, said barrier means being positioned in the tube at a preselected distance from the admitting-emitting port to define a liquid chamber of preselected volume, and piston means for pushing the barrier means form the vent end to push the barrier means to the admitting-emitting end, and to push the preselected volume of liquid out of the liquid chamber, stop means at the admitting-emitting port for preventing discharging the barrier means from the tube, said piston means being a plunger comprising a tube of smaller outside diameter than the inside diameter of the capillary tube, said barrier means being made of a material for passing air freely to vent so as to not impede or delay the capillary action of drawing a liquid into the tube and for stopping passage of air and liquid upon being wetted by the liquid to obtain a preselected volume of liquid in the chamber, said piston means being a plunger positioned in the capillary tube with the barrier means positioned in the head end of the plunger, and the plunger being hollow for passing air freely from the tube to allow for capillary action, said device including temporary sealing means comprising a wax seal connecting the plunger to the vent end of the capillary tube to temporarily hold the barrier means in desired position in the capillary tube to define a liquid chamber of pre-selected volume and to permit breaking the wax seal by pushing the plunger toward the admitting-emitting port.

12. A disposable pre-selected volume capillary pipet device, comprising
    capillary means for drawing liquid by capillary action into a chamber having a pre-selected volume,
    said capillary means including a capillary tube with an admitting-emitting end for admitting liquids by touching said end to a liquid and drawing the liquid into the chamber by capillary action,
    said capillary tube also including a vent end at the other end of the tube for passing air from the tube as the liquid is being drawn into the tube by capillary action,
    a port at the admitting-emitting end for admitting and emitting liquids to the capillary tube,
    a port at the vent end of the tube,
    barrier means for passing air though the tube as the liquid is being drawn into the tube by capillary action and for stopping the passage of liquid through the tube when the liquid touches the barrier means,
    said barrier means being positioned in the tube at a pre-selected distance from the admitting-emitting port to define one end of the liquid chamber of pre-selected volume with the other end of the chamber being defined by the port at the admitting-emitting end,
    and piston means for pushing the barrier means to the admitting-emitting port to push the pre-selected volume of liquid out of the capillary tube,
    said piston means being a plunger comprising a tube which fits inside said capillary tube and is hollow for allowing air to pass freely through the barrier means and the plunger to the vent end of the capillary tube and to permit the drawing of liquid into the tube by capillary action,
    said hollow plunger being seated in the tube and extruding from the vent end thereof during the filling of the chamber with liquid by capillary action.

13. The disposable pre-selected volume capillary pipet device according to claim 12,
    said barrier means fitting tightly within the capillary tube for wiping the walls of the liquid chamber when the piston means is pushing the barrier means.

14. A disposable pre-selected volume capillary pipet device, comprising
    capillary means for drawing liquid by capillary action into a chamber having a pre-selected volume,
    said capillary means including a capillary tube with an admitting-emitting end for admitting liquids by touching said end to a liquid and drawing the liquid into the chamber by capillary action,
    said capillary tube also including a vent end at the other end of the tube for passing air from the tube as the liquid is being drawn into the tube by capillary action,
    a port at the admitting-emitting end for admitting and emitting liquids to the capillary tube,
    a port at the vent end of the tube,
    barrier means for passing air freely through the tube to allow for capillary flow as the liquid is being drawn into the tube by capillary action and for stopping the passage of liquid through the tube when the liquid touches the barrier means,
    said barrier means being positioned in the tube at a pre-selected distance from the admitting-emitting port to define one end of the liquid chamber of pre-selected volume with the other end of the chamber being defined by the port at the admitting-emitting end,
    and piston means for pushing the barrier means to the admitting-emitting port to push the pre-selected volume of liquid out of the capillary tube,
    said barrier means including a material which gels on being wetted by the liquid to form a liquid and air barrier,
    said plunger being of sufficient length to push the barrier means to the port at the admitting-emitting end of the tube,
    said plunger being readily detachable from said barrier means.

15. A disposable preselected-volume capillary pipet device comprising
    capillary means for drawing liquid into a capillary tube by capillary action,
    said capillary means comprising the capillary tube with an admitting-emitting end for liquids and a vent end for passing air from the tube as the liquid is being drawn into the tube by capillary action,
    a port at the admitting-emitting end for admitting and emitting liquids to the capillary tube,
    a port at the vent end of the tube,
    barrier means for passing air and stopping the passage of liquid through the tube,
    said barrier means being positioned in the tube at a preselected distance from the admitting-emitting port to define a liquid chamber of preselected volume,
    said piston means for pushing the barrier means from the vent end to push the barrier means to the admitting-emitting end and to push the preselected volume of liquid out of the liquid chamber,
    said piston means being a plunger comprising a tube of smaller outside diameter than the inside diameter of the capillary tube,
    said barrier means being made of a material for passing air freely to vent so as to not impede or delay the capillary action of drawing a liquid into the tube and for stopping passage of air and liquid upon being wetted by the liquid to obtain a preselected volume of liquid in the chamber,
    said piston means being a plunger positioned in the capillary tube with the barrier means being positioned in the head end of the plunger, and the plunger being hollow for passing air freely from the tube to allow for a capillary flow, and
    said plunger being of sufficient length to push the barrier means to the port at the admitting-emitting end of the tube.

16. The device of claim 15, including
    temporary sealing means comprising a wax seal connecting the plunger to the vent end of the capillary tube to temporarily hold the barrier means in desired position in the capillary tube to define a liquid chamber of preselected volume and to permit breaking the wax seal by pushing the plunger toward or away from the admitting-emitting port.

* * * * *